US009841397B2

(12) United States Patent
Rottmann et al.

(10) Patent No.: US 9,841,397 B2
(45) Date of Patent: Dec. 12, 2017

(54) SENSOR ELEMENT INCLUDING A STRIP CONDUCTOR AND A REFERENCE GAS CHANNEL

(71) Applicant: Robert Bosch GmbH, Stuttgart (DE)

(72) Inventors: Andreas Rottmann, Stettfeld (DE); Frank Buse, Stuttgart (DE); Jens Schneider, Leonberg (DE); Thomas Juestel, Hirschaid-Juliushof (DE)

(73) Assignee: Robert Bosch GmbH, Stuttgart (DE)

( * ) Notice: Subject to any disclaimer, the term of this patent is extended or adjusted under 35 U.S.C. 154(b) by 106 days.

(21) Appl. No.: 14/900,435

(22) PCT Filed: May 14, 2014

(86) PCT No.: PCT/EP2014/059833
§ 371 (c)(1),
(2) Date: Dec. 21, 2015

(87) PCT Pub. No.: WO2014/202287
PCT Pub. Date: Dec. 24, 2014

(65) Prior Publication Data
US 2016/0153929 A1    Jun. 2, 2016

(30) Foreign Application Priority Data
Jun. 21, 2013   (DE) ......................... 10 2013 211 793

(51) Int. Cl.
*G01N 27/00* (2006.01)
*G01N 27/407* (2006.01)
(Continued)

(52) U.S. Cl.
CPC ...... *G01N 27/4071* (2013.01); *G01M 15/104* (2013.01); *G01N 27/12* (2013.01);
(Continued)

(58) Field of Classification Search
CPC .................................................. G01N 27/4077
(Continued)

(56) References Cited

U.S. PATENT DOCUMENTS 4,880,519 A * 11/1989 Wang ................. G01N 27/4067
204/424
4,883,947 A * 11/1989 Murase ............. G01N 27/4067
219/538

(Continued)

FOREIGN PATENT DOCUMENTS

DE    10157733    *  6/2003    .......... G01N 27/407
DE    101 57 733        2/2004
(Continued)

OTHER PUBLICATIONS

Fidelus JD, Lojkowski W, Millers D, Smits K, Grigorjeva L (2009) Advanced Nanocrystalline ZrO2 for optical oxyen sensors, IEEE Sensors 9:1268-1272, 5 pages.*

(Continued)

*Primary Examiner* — Clayton E Laballe
*Assistant Examiner* — Kevin Butler
(74) *Attorney, Agent, or Firm* — Norton Rose Fulbright US LLP; Gerard Messina

(57) ABSTRACT

A sensor element for detecting a physical property of a gas includes: a solid electrolyte film; a first end area and a second end area situated diametrically opposite in the longitudinal direction; a functional element in the first end area in the interior which is electrically conductively connected to a contact surface situated in the second end area on the outer surface, the electrically conductive connection having a strip conductor running essentially in the longitudinal direction in the interior of the sensor element; and a reference gas channel running essentially in the longitudinal direction of the sensor element communicating with a ref- (Continued)

erence gas outside of the sensor element via a reference gas opening, the strip conductor and the reference gas channel being situated in such a way that at least a partial overlap occurs between them.

10 Claims, 6 Drawing Sheets

(51) Int. Cl.
  *G01M 15/10* (2006.01)
  *G01N 27/419* (2006.01)
  *G01N 27/409* (2006.01)
  *G01N 27/26* (2006.01)
  *G01N 27/12* (2006.01)
  *H05B 3/06* (2006.01)
  *G01N 33/00* (2006.01)

(52) U.S. Cl.
  CPC ............ *G01N 27/26* (2013.01); *G01N 27/407* (2013.01); *G01N 27/409* (2013.01); *G01N 27/4077* (2013.01); *G01N 27/419* (2013.01); *G01N 33/0009* (2013.01); *G01N 33/0031* (2013.01); *H05B 3/06* (2013.01)

(58) Field of Classification Search
  USPC ....................................................... 73/31.05
  See application file for complete search history.

(56) References Cited

U.S. PATENT DOCUMENTS

| | | | | |
|---|---|---|---|---|
| 5,948,966 | A * | 9/1999 | Takahashi | F01N 11/00 204/424 |
| 6,153,861 | A * | 11/2000 | Weyl | G01N 27/4067 219/269 |
| 6,303,011 | B1 * | 10/2001 | Gao | G01N 27/4074 204/425 |
| 6,463,789 | B2 * | 10/2002 | Moos | G01N 27/123 324/609 |
| 6,572,747 | B1 * | 6/2003 | Fouts | G01N 27/419 156/89.12 |
| 7,631,539 | B2 * | 12/2009 | Akatsuka | G01N 27/4078 73/31.05 |
| 7,820,949 | B2 * | 10/2010 | Sasaki | G01N 27/16 123/697 |
| 8,038,933 | B2 * | 10/2011 | Weyl | G01N 27/4077 277/650 |
| 9,694,387 | B2 * | 7/2017 | Onkawa | G01N 27/4077 |
| 9,719,957 | B2 * | 8/2017 | Kamada | G01N 27/4071 |
| 2001/0023611 | A1 * | 9/2001 | Matsuo | G01N 27/407 73/31.05 |
| 2002/0112958 | A1 * | 8/2002 | Diehl | G01N 27/4071 204/426 |
| 2008/0016947 | A1 * | 1/2008 | Mizutani | G01N 27/4062 73/31.05 |
| 2009/0071231 | A1 * | 3/2009 | Fujii | G01N 27/4077 73/31.05 |
| 2010/0000293 | A1 * | 1/2010 | Kawai | G01N 27/4071 73/31.05 |
| 2013/0019655 | A1 * | 1/2013 | Nakagawa | G01N 27/419 73/31.05 |
| 2013/0048627 | A1 * | 2/2013 | Satou | H05B 3/06 219/552 |
| 2013/0074582 | A1 * | 3/2013 | Sakuma | G01N 27/4077 73/31.05 |

FOREIGN PATENT DOCUMENTS

| | | | | |
|---|---|---|---|---|
| DE | 10 2005 022135 | | 1/2006 | |
| DE | 102005022135 | * | 1/2006 | ............ G01N 27/26 |
| DE | 10 2006 055797 | | 5/2008 | |
| JP | 2009-133808 | * | 6/2009 | ............ G01N 27/02 |
| WO | WO 2011/153523 | * | 6/2010 | ........... G01N 27/407 |

OTHER PUBLICATIONS

N. Jagadeesh Babu, Design and Development of O2 Gas Sensor Using Metal Oxide Material for Control of the Air-To-Fuel Ratio of InternalCombustion Engines At Low Temperature, IEEE, vol. No. 1, Jan. 2013, 5 pages.*
International Searching Authority, PCT/EP2014/059833 WO2014202287 Written Opinion, Dec. 21, 2015, 6 pages.*
International Searching Authority, PCT/EP2014/059833 WO2014202287 Search Report, Aug. 4, 2014, 2 pages.*
International Search Report for PCT/EP2014/059833, dated Aug. 11, 2014.

* cited by examiner

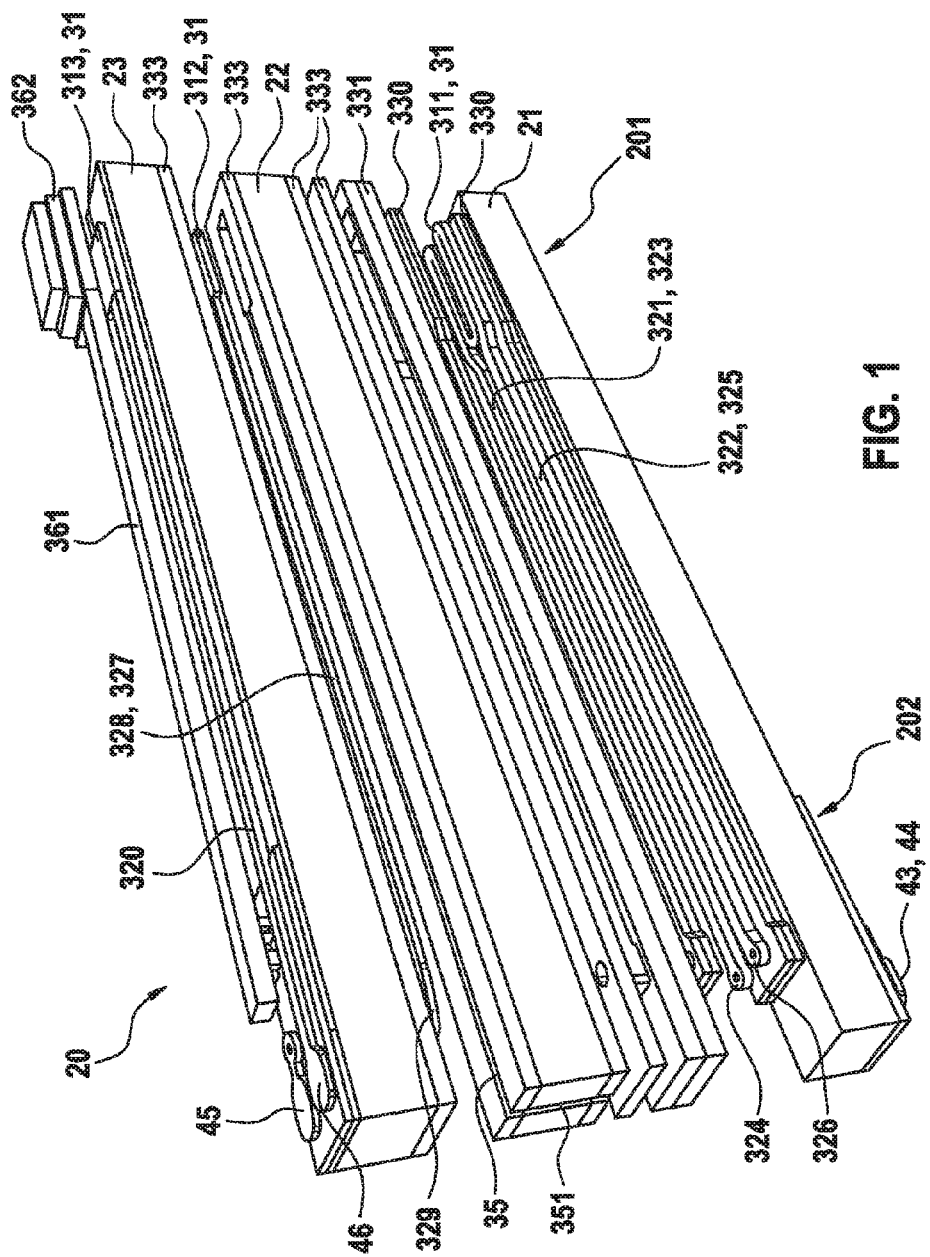

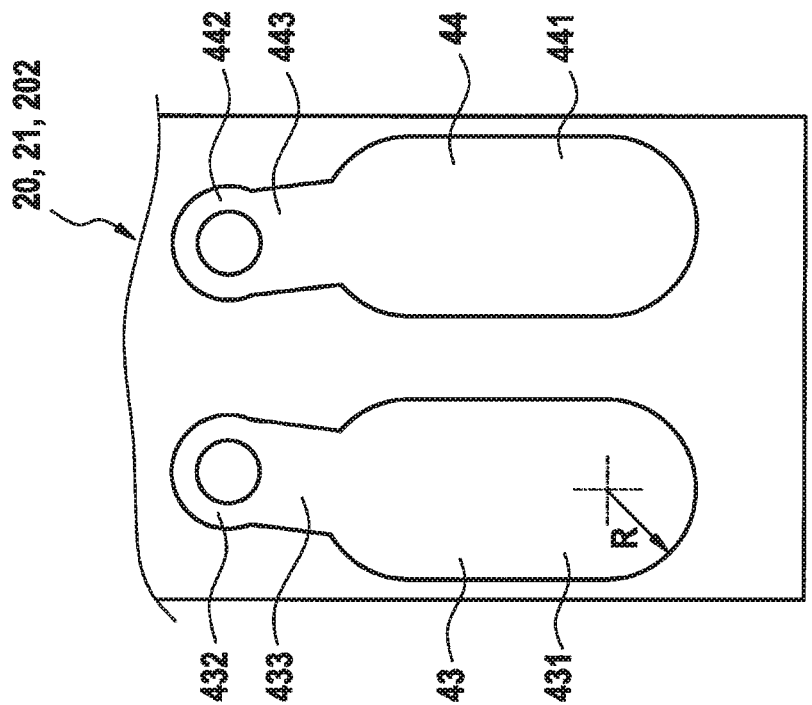
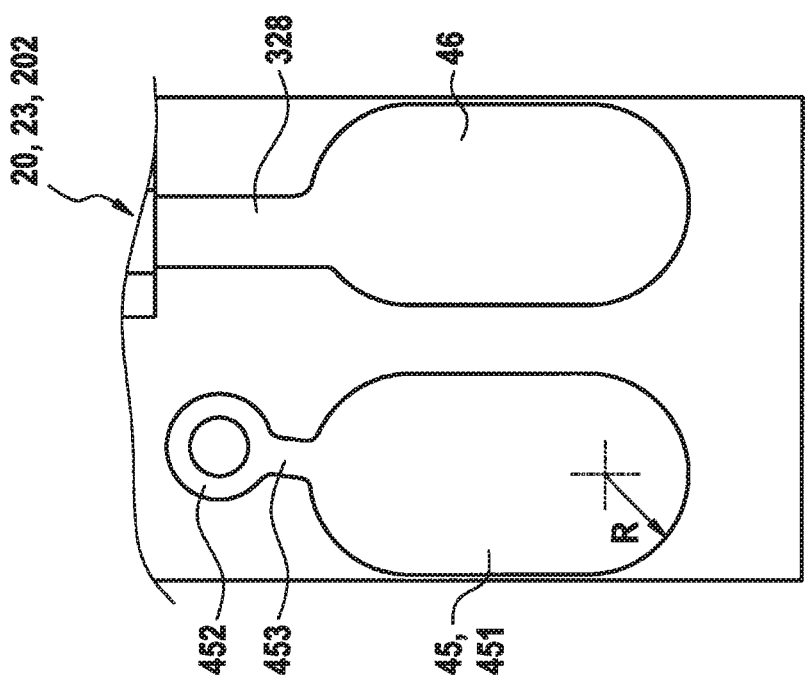

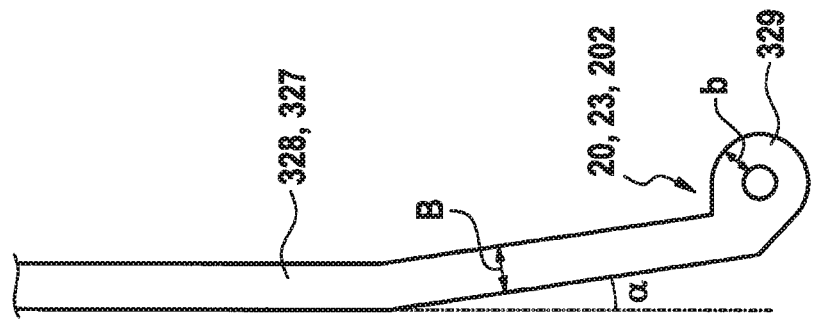
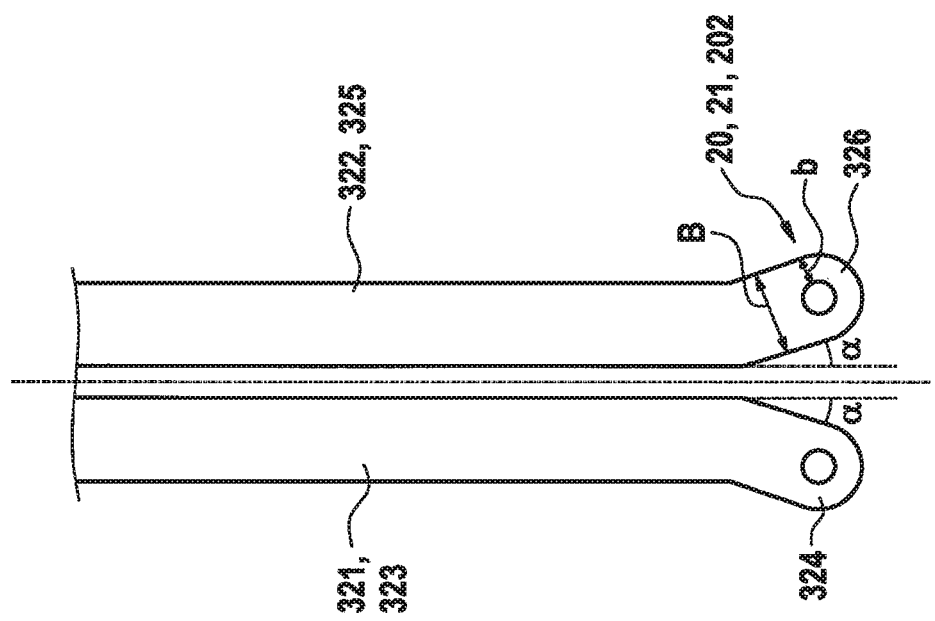

SENSOR ELEMENT INCLUDING A STRIP CONDUCTOR AND A REFERENCE GAS CHANNEL

BACKGROUND OF THE INVENTION

1. Field of the Invention

The present invention is directed to known sensor elements, which are used for example as exhaust gas sensors, in particular as lambda sensors, which have gained an extensive prevalence in motor vehicles. The present invention is, however, also applicable in other types of sensor elements, for example in sensors for detecting other gaseous components of exhaust gases and in particle sensors or the like. The present invention relates in particular to a sintered or sinterable ceramic sensor element which is manufactured for example by combining, in particular by stacking, individual, possibly printed, ceramic green sheets. The present invention further relates in particular to a sensor element in the interior of which a reference gas channel is formed.

2. Description of the Related Art

The sensor element of the type described above further includes in particular at least one electrical, electrochemical, and/or electronic functional element in a first end area of the sensor element generally facing the exhaust gas. An electrical supply to the sensor element is provided in the present case by a contact surface on the outer surface of the sensor element in a second area generally facing away from the exhaust gas.

An electrical supply to the sensor element is carried out in this case by an electrical connection of the functional element to the contact surface, which has a strip conductor running essentially in the longitudinal direction of the sensor element in the interior of the sensor element.

To prevent distortion due to sintering and to optimize the thermal conduction in the interior of the sensor element during operation, it is attractive to configure the strip conductor to overlap completely or partially (for example at least 10% of the width) with the reference gas channel in a top view of the sensor element. The effects in particular of the low sintering shrinkage and the low thermal conduction of a completely or partially unfilled reference gas channel may hereby be compensated for with respect to the entire sensor element.

It is problematic that, due to the aforementioned measures, an edge of the reference gas channel overlaps with the strip conductor in a top view of the sensor element, and thus in the sense of a cutting edge may potentially cause a squeezing of the strip conductor in this area during the manufacturing process.

Sensor elements of this type are known for example from German patent document DE 101 57 733 B4.

BRIEF SUMMARY OF THE INVENTION

Sensor elements according to the present invention have the advantage over the related art that the area, in which an edge of the reference channel overlaps with the strip conductor in a top view of the sensor element, extends relatively far in the longitudinal direction of the sensor element. The potential cutting effect of the edge of the reference gas channel is thus distributed across this broad extension and, as a result, a squeezing of the strip conductor in this area emerges to a disproportionately lesser degree.

For this purpose, it is provided according to the present invention that the strip conductor runs at an angle α of not more than 25°, in particular not more than 14°, to the outer side of the sensor element 20° at its end facing away from the first end area of the sensor element.

To not unnecessarily reduce the area, in which the strip conductor is configured to completely or partially overlap with the reference gas channel in a top view of the sensor element, in its length and/or width, a lower limit may in particular also be provided for angle α, which it should not fall short of, and which may be for example 2° or 5°.

The area in which the strip conductor runs at an angle preferably has a minimum extension in the longitudinal direction, which may be for example 2 mm, 3 mm, or even 4 mm, or may be defined by the width of the strip conductor.

The lateral offset, caused by the angle, at the end of the strip conductor facing away from the first end area of the sensor element arises in particular as a product of the extension of the area, in which the strip conductor runs at an angle, and the inverse tangent of angle α. It is preferred that this lateral offset is not less than half or the full width of the overlap between the strip conductor and the reference gas channel. The preferred offset may also be in particular not less than 0.3 mm or not less than 0.5 mm.

In special specific embodiments of the present invention, the reference gas channel is unfilled, thus forming in particular a cavity designed macroscopically in relation to the sensor element and having, for example, a rectangular cross section. In this case, while on the one hand the access of reference air to the sensor element is basically improved, the above-mentioned problem of the potential cutting effect of the edge of the reference gas channel is, however, initially even exacerbated.

In special specific embodiments of the present invention, the electrically conductive connection between the functional element and the contact surface has a feedthrough in addition to the strip conductor, with which the feedthrough interacts, and the feedthrough runs essentially perpendicularly to the longitudinal direction of the sensor element. The feedthrough includes in particular a conductive coating of the radial wall of a via hole of the sensor element. The reference gas channel is situated in particular without overlap of the feedthrough, in a top view of the sensor element, which results in the advantage that the breaking strength of the sensor element is only slightly reduced by the feedthrough.

Insofar as this concerns a strip conductor, it may in the present case include a feed line and a collar, the collar may be situated on the feed line facing away from the exhaust gas, the feed line may have entirely or at least in its part facing away from the exhaust gas a constant width, and/or the collar may have a ring-shaped, for example an annular, design.

The end of the strip conductor facing away from the first end area of the sensor element may also in particular be defined by the end of the feed line facing away from the first end area of the sensor element and/or by the totality formed by the end of the feed line facing away from the first end area of the sensor element plus the collar of the strip conductor.

The terms "longitudinal direction," "transverse direction," and "vertical direction" are basically used in the context of this application in the sense of a rectangular reference system. In particular, they may, however, additionally be directions which are distinguished by the sensor element, for example, in an in particular ashlar shaped sensor element, the longitudinal direction may be the direction in which the longest side edges of the sensor element point, the vertical direction may be the direction in which the shortest side edges of the sensor element point, and/or the transverse direction may be the direction in which the side edges of the sensor element point which have a middle length. For example, in a rod-shaped sensor element, the longitudinal direction may point in the direction of an axis around which the rod-shaped sensor element is rotationally symmetrical or is essentially rotationally symmetrical.

Where reference is only essentially made to a direction, directions are considered, in addition to the direction in the narrow meaning, which deviate slightly from this direction, for example by not more than 15°, and/or directions that are at least not orthogonal to this direction. A direction is also essentially realized by a structure if the affected structure only deviates in a small subarea, which for example does not include more than 10% of the structure.

"Length of the sensor element" is understood to mean the extension of the sensor element in the longitudinal direction, "width of the sensor element" is understood to mean the extension of the sensor element in the transverse direction, and "height of the sensor element" is understood to mean the extension of the sensor element in the vertical direction within the context of this application. This direction is also applicable for the top view of the sensor element.

The term "end area of the sensor element" is understood to mean basically only a cohesive subarea of the sensor element with respect to a longitudinal direction within the context of this application, and includes the affected end of the sensor and does not amount to more than 50% of the length of the sensor element. In this respect, one end area intersects with a diametrically opposite end area only in a flat expanse, for example. In a somewhat more limited way, an end area of the sensor element may be understood in particular as a cohesive subarea of the sensor element which includes the affected end of the sensor and does not amount to more than one-third or even not more than one-fourth of the length of the sensor element.

The term "functional element" is in the present case basically not to be interpreted narrowly. For example, it may be a precious metal electrode or cermet electrode communicating with the exterior space of the sensor element, and/or an electrical resistance heater which has in particular an electrical resistance of a maximum of 30 Ohm at 20° C., and/or the like.

In the case of the resistance heater as the functional element, two strip conductors of the presently described specific embodiments may be provided positioned side by side, in particular in mirror symmetry.

In the case of the cermet electrode as the functional element, the strip conductor or feed line to this cermet electrode may be situated in particular directly diametrically opposite to the reference gas channel. For this reason, it may be advantageous that this strip conductor or feed line has a width in the area, in which it runs at an angle, and/or in the area in which it intersects an edge of the reference gas channel, in a top view of the sensor element, which is increased with respect to an area of the strip conductor (or feed line) facing the exhaust gas, in particular by at least 25% or by at least 0.1 mm.

In conjunction with the present invention, a specific material selection for strip conductors, feed lines, feedthroughs, and contact surfaces may be additionally constructive. Basically, materials with a precious metal proportion of 83 wt. % or more are hereby preferred, so that predefined ohmic resistances may be achieved at minimized use of precious metals. For at least one feed line to the heating device, even precious metal proportions of 95 wt. % or more, for example 98 wt. %, are preferred. A proportion of at least 1 wt. % of Al2O3, even better at least 1.5 wt. % of Al2O3, preferably a maximum of 2.5 wt. % of Al2O3, has been proven as favorable for the precise adjustability of the electrical resistance of these structures.

At least one feed line to the heating device may be configured integrally with the heating device and made from the same material.

In addition or alternatively, a lower precious metal proportion, than is provided for the at least one feed line to the heating device, is provided for the feed line to the cermet electrode and/or for at least one contact surface, preferably for example 83 wt. % through 87 wt. %, in particular a proportion of ZrO2 and Y2O3 together of 12 wt. % through 16 wt. % being provided in the feed line to the cermet electrode.

It is advantageous that the feed line to the cermet electrode may be manufactured together with the cermet electrode in one process step and made from the same material. For the feed line to the cermet electrode or for the cermet electrode, a proportion of Al2O3 of preferably 0.2 wt. % through 1 wt. % is also advantageous.

In addition or alternatively, a lower precious metal proportion, than is provided for the at least one feed line to the heating device, is provided for the at least one feed through, preferably for example 83 wt. % through 87 wt. %, a proportion of ZrO2 and Y2O3 together of 3 wt. % through 8 wt. % and additionally a proportion of Nb2O5 of 6 wt. % through 12 wt. % being provided in the feedthrough. It is advantageous that the feedthroughs are easier to manage handle during the manufacturing process. In particular, corresponding pastes have better rheological characteristics and enable a better ceramic linking of the feedthroughs within the sensor element. In conjunction with sensor elements, which are made predominantly from YSZ, a reduced oxygen ion conductivity is moreover formed in the border areas of the feedthroughs, which improves the functionality of the sensor elements.

The above-mentioned precious metal proportions may include in particular platinum. Alternatively, in particular with respect to at least one feedthrough, proportions of rhodium may be included to stabilize the metal phase, preferably 0.2 wt. % through 0.8 wt. % relative to the total composition of the materials, and/or proportions of palladium, preferably 0.2 wt. % through 1 wt. % relative to the total composition of the materials, may be included.

Additional proportions of precious metals may always be provided.

BRIEF DESCRIPTION OF THE DRAWINGS

FIG. 1 shows a sensor element according to the present invention perspectively and schematically in an exploded view.

FIG. 2 shows second end area 202 of sensor element 20 facing away from the exhaust gas in a top view of third solid electrolyte film 23.

FIG. 3 shows second end area 202 of sensor element 20 facing away from the exhaust gas in a bottom view to below first solid electrolyte film 21 facing downward in FIG. 1.

FIG. 4 shows second end area 202 of sensor element 20 facing away from the exhaust gas in a top view of first solid electrolyte film 21, from above in FIG. 1.

FIG. 5 shows second end area 202 of sensor element 20 facing away from the exhaust gas in a bottom view to below first solid electrolyte film 23 from below in FIG. 3.

DETAILED DESCRIPTION OF THE INVENTION

Figure 5A:
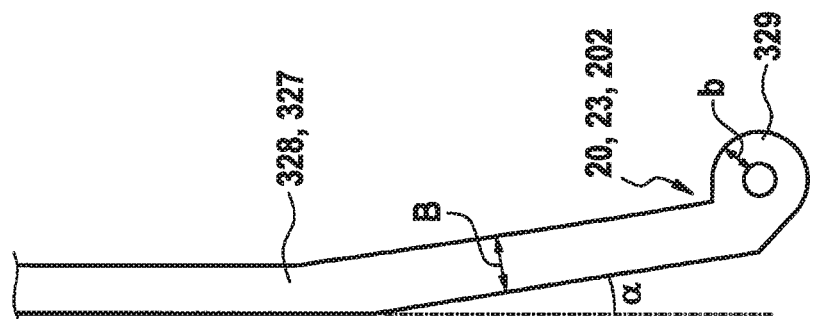
FIG. 5a shows as a variant a sensor element 20 with slightly modified feed line 328.

FIG. 1 shows, as an exemplary embodiment of the present invention, a general view of a sensor element 20, which may be situated in a housing of a gas sensor (not shown) which is used for determining the oxygen concentration in an exhaust gas of an internal combustion engine (not shown). Provided with corresponding functional elements, the present invention is of course also suited for sensor elements in other sensors, for example sensors for particle measurement.

The sensor element extends in FIG. 1 in the longitudinal direction from left to right, a first end area 201 of sensor element 20 being mapped on the right and a second end area 202 of sensor element 20 being mapped on the left. In intended installation and operation, first end area 201 of sensor 20 faces an exhaust gas and second end area 202 of sensor element 20 faces away from the exhaust gas.

Sensor element 20 in FIG. 1 additionally extends in the transverse direction from front to back and in the vertical direction from bottom to top.

Sensor element 20 is constructed from printed ceramic layers which are formed in this example as a first, second, and third solid electrolyte film 21, 22, 23 and contain zirconium oxide stabilized by yttrium oxide (yttria-stabilized zirconia, YSZ). Solid electrolyte films 21, 22, 23 have, prior to a sintering process in the example, a length of 72 mm, a width of 5 mm, and a height of 540 µm. Films of a sintered sensor element 20 have an edge length reduced by 20%.

First solid electrolyte film 21 is provided on its large surface facing outward, downward from the perspective of sensor element 20 in FIG. 1, in second end area 202 of sensor element 20 with a contact surface 43 and an additional contact surface 44, printed in this case; see also FIG. 3.

First solid electrolyte film 21 is provided on its large surface facing inward, upward from the perspective of sensor element 20 in FIG. 1, in first end area 201 of sensor element 20 with a meander-shaped heating device 311 as a functional element 31 which is used for heating first end area 201 of sensor element 20. In a continuation of meander-shaped heating device 311, a strip conductor 321, 322 is connected to its respective ends, the transition from heating device 311 to strip conductor 321, 322 being characterized by an increase in the structural width and/or height or by a reduction of the electrical resistance per length.

Strip conductors 321, 322 have on the exhaust gas side a section, designated as feed line 323, 325 which in the present case has a constant width. Strip conductors 321, 322 additionally have a section facing away from the exhaust gas designated as collar 324, 326, which in the present case has a ring-shaped design; see also FIG. 4.

First solid electrolyte film 21 is additionally provided on its large surface facing inward, upward from the perspective of sensor element 20 in FIG. 1, with insulation layers 330 and a sealing frame 331, and also a film binder layer 333, printed in this case.

Figure 6:
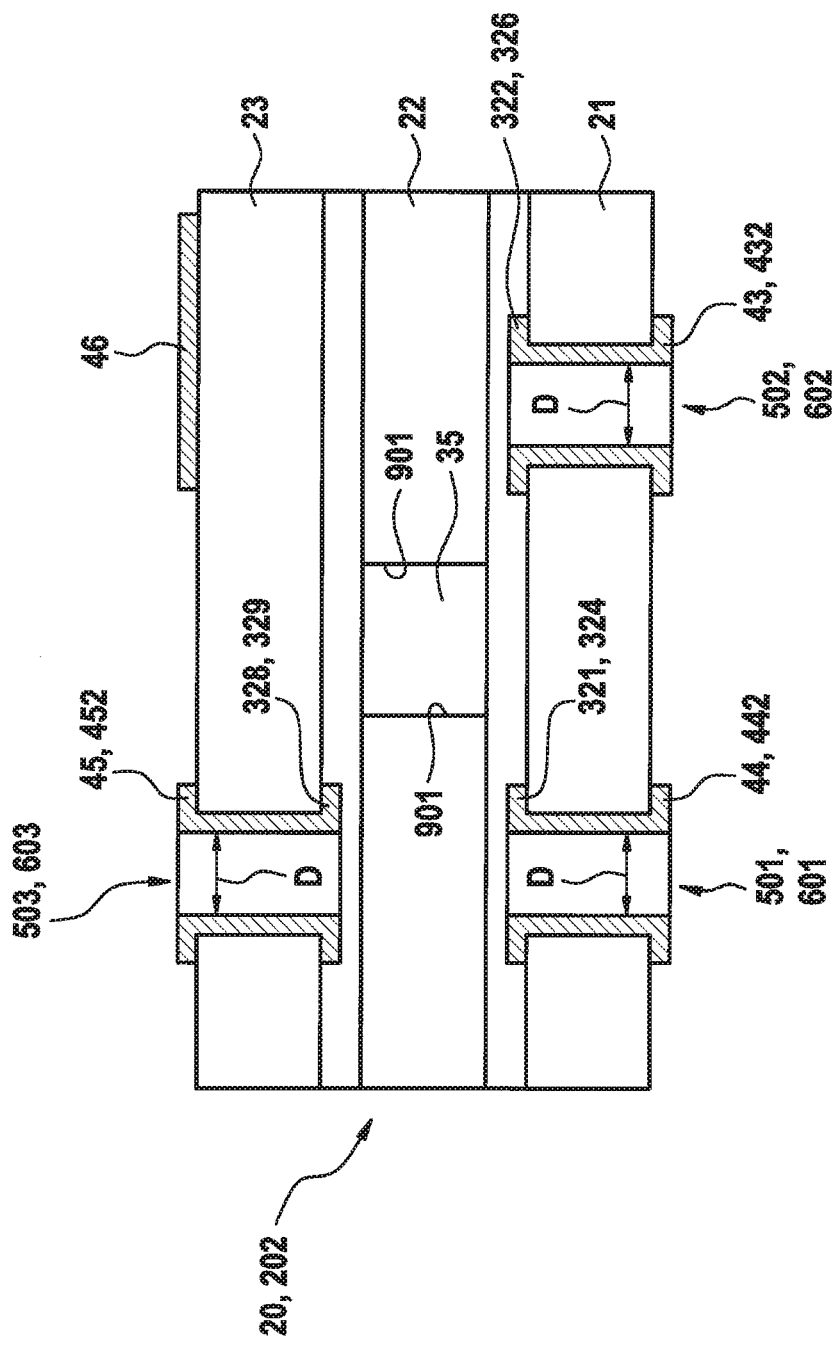
FIG. 6 shows a purely schematic section through sensor element 20 shown in the preceding FIGS. 1 through 5, in a plane perpendicular to the longitudinal direction of sensor element 20 through feedthroughs 501, 502, 503.

First solid electrolyte film 21 has in second end area 202 two feedthroughs 501, 502 which extend in the vertical direction through first solid electrolyte film 21 and each electrically conductively connect a contact surface 43, 44 to a collar 324, 326 of a strip conductor 321, 322; see FIG. 6.

Second solid electrolyte film 22 is provided on both sides with a film binder layer 333; second solid electrolyte film 22 additionally has a reference gas channel 35 which extends longitudinally from a reference gas opening 351 situated facing away from the exhaust gas to first end area 201 of sensor element 20 and thereby runs centrically in the transverse direction. Reference gas channel 35 is designed as unfilled, in particular no porous fillings are provided in it.

Third solid electrolyte film 23 is provided on its large surface facing inward, downward from the perspective of sensor element 20 in FIG. 1, with a cermet electrode 312 as functional element 31 for measuring an oxygen concentration diametrically opposite to reference gas channel 35. In a continuation of cermet electrode 312, a strip conductor 328 is connected to the end of cermet electrode 312, the transition from the cermet electrode to strip conductor 328 being characterized by a reduction of the structural width.

Strip conductor 328 has a section on the exhaust gas side designated as feed line 327 which in the present case has a constant width. Strip conductor 328 additionally has a section facing away from the exhaust gas designated as collar 329 which has a ring-shaped design in the present case; see also FIG. 5. A film binder layer 333 is provided on this side of third solid electrolyte film 23, at least where it is otherwise plain.

Third solid electrolyte film 23 is provided on its large surface facing outward, upward from the perspective of sensor element 20 in FIG. 1, in second end area 202 of sensor element 20 with a contact surface 45 and an additional contact surface 46, printed in the present case; see also FIG. 2.

A strip conductor 320, with for example a constant width, connects to additional contact surface 46 and extends to an additional cermet electrode 313 situated in first end area 201 of sensor element 20. Strip conductor 320 is covered for example with a dense cover layer 361; additional cermet electrode 313 is provided with porous layers 362 so that a communication between the exterior space and additional cermet electrode 313 is ensured.

Third solid electrolyte film 23 has in the second end area a feedthrough 503 which extends in the vertical direction through third solid electrolyte film 23 and electrically conductively connects contact surface 45 to collar 329; see FIG. 6.

FIG. 2 shows second end area 202 of sensor element 20 facing away from the exhaust gas in a top view of third solid electrolyte film 23. Contact surface 45 is situated on the left there when viewed toward first end area 201 of sensor 20 facing the exhaust gas.

Contact surface 45 is composed of three subareas, namely a trunk area 451, a head area 452, and a neck area 453. Trunk area 451 is situated on the side of contact surface 45 facing away from the exhaust gas. It has an elongated base shape which arises from a rectangle with equal length and width through maximum rounding of the corners, i.e., through a rounding at a radius of curvature R which corresponds to half of the width of trunk area 451 or contact surface 45. In this way, semicircular end areas of trunk area 451 or contact surface 45 are thus created on the side of contact surface 45 facing away from the exhaust gas.

Based on an unsintered sensor element 20 (sintered: −20%), the length of trunk area 451 in this example is 2.5 mm or more; the width or trunk area 451 is 1.5 mm or more. Trunk area 451 is spaced at a distance of 0.4 mm or less from the left outer edge of sensor element 20 and is spaced at a distance of 1.3 mm or less from the front outer edge of sensor element 20.

Head area 452 is situated on the side of contact surface 45 facing the exhaust gas. Head area 452 has, for example, a ring-shaped design with an inner diameter of 0.5 mm or less and an outer diameter of 1 mm or more based on an unsintered sensor element 20 (sintered: −20%).

Neck area 453 is formed between trunk area 451 and head area 452. It forms a constriction of contact surface 45 with respect to trunk area 451 and head area 452 and has a minimum width in the example of 0.3 mm and a length of 0.3 mm based on an unsintered sensor element 20 (sintered: −20%).

Trunk area 451 in the example has a mirror symmetry with respect to an axis which points in the longitudinal direction of sensor element 20. Head area 452 and neck area 453 likewise have a mirror symmetry; however, with respect to an axis which is rotated by 9° in the mathematically negative direction of rotation in a top view of sensor element 20 with respect to the longitudinal axis of sensor element 20 so that head area 452 and neck area 453 are, as a whole, slightly tilted toward the center of the sensor.

Head area 452 of contact surface 45 interacts electrically conductively with a feedthrough 503 through third solid electrolyte film 23.

Moreover, additional contact surface 46 is situated to the right adjacent to contact surface 45 in FIG. 2 when viewed toward first end area 201 of sensor element 20 facing the exhaust gas. The arrangement and the size of additional contact surface 46 correspond in this sense, i.e., by interchanging left and right, to the arrangement and the size of trunk area 451 of contact surface 45 providing that a distance of at least 0.6 mm exists between contact surface 45 and additional contact surface 46, based on an unsintered sensor element 20 (sintered: −20%).

Additional contact surface 46 includes only one part corresponding to trunk area 451 of contact surface 45, thus has neither head- nor neck area. It also does not interact with a feedthrough; instead, it is directly contacted to strip conductor 328 which leads to additional cermet electrode 313. A center axis of strip conductor 328 is displaced transversely inward in the longitudinal direction, with respect to a center axis of additional contact surface 46, by 0.1 mm to 0.4 mm, in the example by 0.2 mm, based on an unsintered sensor element 20 (sintered: −20%).

Contact surfaces 45, 46 have a precious metal proportion of 83 wt. % through 87 wt. %, and a proportion of ZrO2 and Y2O3 together of 12 wt. % through 16 wt. %.

FIG. 3 shows second end area 202 of sensor element 20 facing away from the exhaust gas in a bottom view to below first solid electrolyte film 21 facing downward in FIG. 1. Contact surface 43 is situated on the left there when viewed toward first end area 201 of sensor element 20 facing the exhaust gas.

Contact surface 43 is composed of three subareas, namely a trunk area 431, a head area 432, and a neck area 433. Trunk area 431 is situated on the side of contact surface 43 facing away from the exhaust gas. It has an elongated base shape which arises from a rectangle with equal length and width through maximum rounding of the corners, i.e., through a rounding at a radius of curvature R which corresponds to half of the width of trunk area 431 or contact surface 43. In this way, semicircular end areas of trunk area 431 or contact surface 43 are thus created on the side of contact surface 43 facing away from the exhaust gas.

Based on an unsintered sensor element 20 (sintered: −20%), the length of trunk area 431 in this example is 2.5 mm or more; the width or trunk area 431 is 1.5 mm or more. Trunk area 431 is spaced at a distance of 0.4 mm or less from the left outer edge of sensor element 20 and is spaced at a distance of 1.3 mm or less from the front outer edge of sensor element 20.

Head area 432 is situated on the side of contact surface 43 facing the exhaust gas. Head area 432 has a ring-shaped design, for example, with an inner diameter of 0.5 mm or less and an outer diameter of 1 mm or more based on an unsintered sensor element 20 (sintered: −20%).

Neck area 433 is formed between trunk area 431 and head area 432. It forms a constriction of contact surface 43 with respect to trunk area 431 and head area 432 and has a minimum width in the example of 0.9 mm and a length of 0.3 mm based on an unsintered sensor element 20 (sintered: −20%).

Neck area 433 of contact surface 43 is substantially wider, in this case by a factor of 2, than neck area 451 of contact surface 45 in FIG. 2. The background is that high currents are supplied to heating device 311 via contact surface 43, whereas only comparatively low currents are supplied to cermet electrode 312 via contact surface 45. Contact surface 43 is consequently provided with a reduced ohmic resistance or a widened neck area 433.

Trunk area 431 in the example has a mirror symmetry with respect to an axis which points in the longitudinal direction of sensor element 20. Head area 432 and neck area 433 likewise have a mirror symmetry; however, with respect to an axis which is rotated by 9° in the mathematically negative direction of rotation in a top view of sensor element 20 with respect to the longitudinal axis of sensor element 20 so that head area 432 and neck area 433 are, as a whole, slightly tilted toward the center of the sensor.

Head area 432 of contact surface 43 interacts electrically conductively with a feedthrough 501 through first solid electrolyte film 21.

Moreover, additional contact surface 44 is situated to the right adjacent to contact surface 43 in FIG. 3 when viewed toward first end area 201 of sensor element 20 facing the exhaust gas. The arrangement and the size of additional contact surface 46 correspond in this sense, i.e., by interchanging left and right and positive direction of rotation with negative direction of rotation, to the arrangement and the size of contact surface 43 providing that a distance of at least 0.6 mm exists between contact surface 43 and additional contact surface 44, based on an unsintered sensor element 20 (sintered: −20%).

Contact surfaces 43, 44 have a precious metal proportion of 83 wt. % through 87 wt. %, and a proportion of ZrO2 and Y2O3 together of 12 wt. % through 16 wt. %.

FIG. 4 shows second end area 202 of sensor element 20 facing away from the exhaust gas in a top view of first solid electrolyte film 21, from above in FIG. 1. Strip conductor 322 is situated to the right when viewed toward first end area 201 of sensor element 20 facing the exhaust gas. Strip conductor 322 is composed of two subareas, namely a feed line 325 and a collar 326.

Feed line 325 forms the exhaust gas side part of strip conductor 322 and extends from heating device 311 on the exhaust gas side to collar 326 situated on feed line 325 facing away from the exhaust gas. In the present case, feed line 325 has a width B of 1.2 mm and runs on the exhaust gas side with a spacing in the transverse direction of 0.25 mm from the central longitudinal axis of sensor element 20, respectively based on an unsintered sensor element 20 (sintered: −20%). In an end area facing away from the exhaust gas, feed line 325 is angled toward the right, i.e., toward the outside, at an angle of 18°.

Collar 326 has a ring-shaped design and describes in the present case an arc of 180°, the outer diameter of which is identical to width B of feed line 325 and its inner diameter is 0.4 mm. A width of the collar is thus 0.3 mm, each based on an unsintered sensor element 20 (sintered: −20%). A width ratio of collar width b to feed line width B is 0.33.

The electrical resistance of feedthrough 501 is the same or approximately the same as the electrical resistance of strip conductor 322, relative to a temperature distribution which may occur or may typically occur during operation of the sensor. In addition to a homogeneous temperature distribution, for example 20° C., alternative temperature distributions which are inhomogeneous are also conceivable here. For example, uniform temperature increases in the longitudinal direction of 1100° C. in the area of heating device 311 and 200° C., 300° C., or even 400° C. in the area of feedthrough 501 may be taken as a basis.

The electrical resistance of the electrical connection of the functional element, in particular heating device 311, to contact surface 43, is in the range of 2.5 Ohms at 20° C., for example.

Moreover, strip conductor 321 is situated symmetrically to strip conductor 322 relative to the central longitudinal axis in FIG. 4 when viewed toward first end area 201 of sensor element 20 facing the exhaust gas. The arrangement and the size of strip conductor 321 correspond in this sense, i.e., by interchanging left and right, to the arrangement and the size of strip conductor 322.

Feed lines 325, 323 have a precious metal proportion of more than 95 wt. %, for example 98 wt. %, and at least 1 wt. % of Al2O3.

The electrical resistance of feedthrough 502 is the same or approximately the same as the electrical resistance of strip conductor 321, relative to a temperature distribution which may occur or may typically occur during operation of the sensor. In addition to a homogeneous temperature distribution, for example 20° C., alternative temperature distributions which are inhomogeneous are also conceivable here. For example, uniform temperature increases in the longitudinal direction of 1100° C. in the area of heating device 311 and 200° C., 300° C., or even 400° C. in the area of feedthrough 501 may be taken as a basis.

Figure 4A:
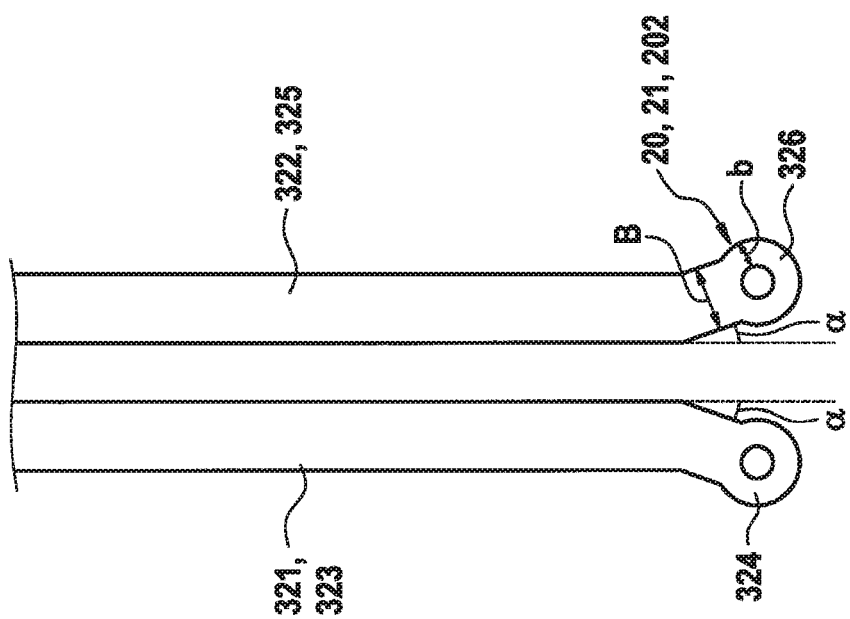
FIG. 4a shows as a variant a sensor element 20 with slightly modified feed lines 323, 325.

FIG. 4a shows as a variant a sensor element 20 with slightly modified feed lines 323, 325, the modification consisting merely in that width B of feed lines 323, 225 is only 1.08 mm instead of 1.2 mm, thus slightly (10%) reduced in comparison to collar 324, 326. The metric dimensions are based on an unsintered sensor element 20 (sintered: −20%).

FIG. 5 shows second end area 202 of sensor element 20 facing away from the exhaust gas in a bottom view to below first solid electrolyte film 23 from below in FIG. 3. Strip conductor 322 is situated to the right when viewed toward first end area 201 of sensor element 20 facing the exhaust gas. Strip conductor 322 is composed of two subareas, namely a feed line 327 and a collar 329.

Feed line 327 forms the exhaust gas side part of the strip conductor and extends from cermet electrode 312 on the exhaust gas side to collar 329 situated on feed line 327 facing away from the exhaust gas. In the present case, the feed line has a width B of 0.4 mm (unsintered; sintered: −20%) and runs on the exhaust gas side so that it is situated within reference gas channel 35 in a vertical projection in a top view of sensor element 20. This part of feed line 327 is thus largely protected from squeezing during the manufacturing process.

In an end area facing away from the exhaust gas, feed line 327 is angled toward the right, i.e., toward the outside, at an angle of not more than 25°, here 8°. In this end area facing away from the exhaust gas, the feed line intersects with the edge of reference gas channel 35 in a vertical projection in a top view of sensor element 20. Due to the comparatively small intersecting angle, a large overlapping zone results between strip conductor 328 and the edge of reference gas channel 35, and thus in turn a good protection from squeezing feed line 327 during the manufacturing process.

Collar 329 has a ring-shaped design. A width of the collar b is 0.3 mm, based on an unsintered sensor element 20 (sintered: −20%). A width ratio of collar width b to feed line width B is 0.75.

Feed line 327 has a precious metal proportion of 83 wt. % through 87 wt. %, and a proportion of ZrO2 and Y2O3 together of 12 wt. % through 16 wt. %.

The electrical resistance of feedthrough 503 is the same or approximately the same as the electrical resistance of strip conductor 328, relative to a temperature distribution which may occur or may typically occur during operation of the sensor. In addition to a homogeneous temperature distribution, for example 20° C., alternative temperature distributions which are inhomogeneous are also conceivable here. For example, uniform temperature increases in the longitudinal direction of 750° C. in the area of cermet electrode 312 and 200° C., 300° C., or even 400° C. in the area of feedthrough 503 may be taken as a basis.

FIG. 5a shows as a variant a sensor element 20 with slightly modified feed line 328, the modification consisting merely in that width B of feed line 328 is increased by 50%, from 0.4 mm to 0.6 mm, in the end area facing away from the exhaust gas with respect to the area of feed line 328 facing the exhaust gas. The metric dimensions are based on an unsintered sensor element 20 (sintered: −20%).

FIG. 6 shows a purely schematic section through sensor element 20 shown in the preceding FIGS. 1 through 5, in a plane perpendicular to the longitudinal direction of sensor element 20 through feedthroughs 501, 502, 503.

Feedthroughs 501, 502, 503 are designed as a conductive coating of the radial wall of a via hole 601, 602, 603 of sensor element 20. The diameter of via holes 601, 602, 603 is 0.6 mm in the example based on an unsintered sensor element 20 (sintered: −20%, i.e., 0.48 mm).

Each of feedthroughs 501, 502, 503 is apparently designed to be without overlap with reference gas channel 35 in a top view of sensor element 20.

Feedthroughs 501, 502, 503 have a precious metal proportion of 83 wt. % through 87 wt. %, and a proportion of ZrO2 and Y2O3 together of 3 wt. % through 8 wt. % and additionally a proportion of Nb2O5 of 6 wt. % through 12 wt. %.

Figure 7:
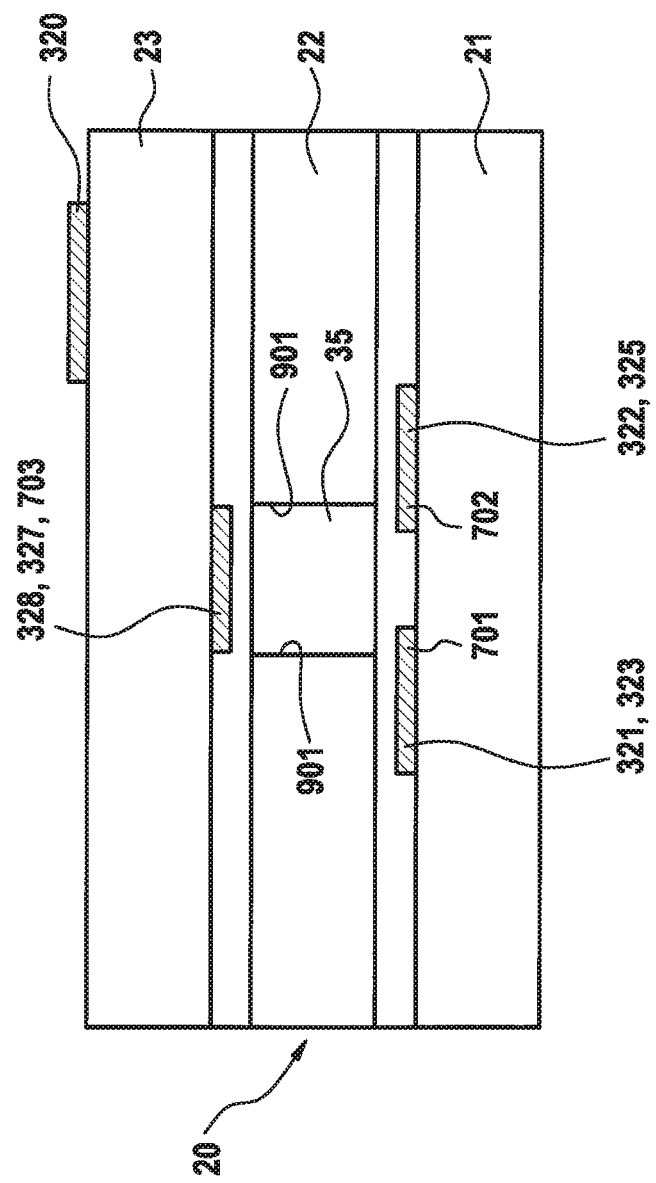
FIG. 7 shows a purely schematic profile section through sensor element 20 shown in the preceding FIGS. 1 through 5, in a plane perpendicular to the longitudinal direction of sensor element 20 approximately in the area of half of the longitudinal extension of sensor element 20.

FIG. 7 shows a purely schematic profile section through sensor element 20 shown in the preceding FIGS. 1 through 5, in a plane perpendicular to the longitudinal direction of sensor element 20 approximately in the area of half of the longitudinal extension of sensor element 20.

As is apparent, in a top view of sensor element 20, strip conductor 328 and feed line 327, which lead to cermet electrode 312, have an overlap 703 across its full width with reference channel 35. Additionally, strip conductors 321, 322 and feed lines 323, 325, which lead to the resistance heater, have an overlap 701, 702 across approximately 10% of their respective widths with reference channel 35.

What is claimed is:

1. A sensor element for detecting a physical property of a gas, comprising:
a first end area and a second end area situated diametrically opposite in the longitudinal direction of the sensor element;
a functional element in the first end area in the interior of the sensor element which is electrically conductively connected to a contact surface situated in the second end area on the outer surface of the sensor element, the electrically conductive connection between the functional element and the contact surface having a strip conductor running essentially in the longitudinal direction in the interior of the sensor element;
a reference gas channel running essentially in the longitudinal direction of the sensor element and communicating with a reference gas outside of the sensor element via a reference gas opening;
wherein the strip conductor and the reference gas channel are situated in such a way that at least a partial overlap occurs between the strip conductor and the reference gas channel when viewed in a top view of the sensor element, and wherein the strip conductor, at an end of the strip conductor that is opposite in the longitudinal direction to the first end area of the sensor element, runs at an angle of more than 0° relative to the outside of the sensor element and not more than 25° relative to the outer side of the sensor element.

2. The sensor element as recited in claim 1, wherein the electrically conductive connection between the functional element and the contact surface has a feedthrough which runs essentially perpendicularly to the longitudinal direction of the sensor element, the feedthrough including a conductive coating of the radial wall of a via hole of the sensor element, and the reference gas channel being situated without overlap with the feedthrough when viewed in the top view of the sensor element.

3. The sensor element as recited in claim 2, wherein the functional element is a two-dimensionally configured cermet electrode which communicates with the exterior space of the sensor element via the reference gas channel.

4. The sensor element as recited in claim 2, wherein the reference gas channel is provided unfilled.

5. The sensor element as recited in claim 2, wherein the functional element is an electric resistance heater which has an electrical resistance of a maximum of 30 Ohms at 20° C.

6. A sensor element for detecting a physical property of a gas, comprising:
a first end area and a second end area situated diametrically opposite in the longitudinal direction of the sensor element;
a functional element in the first end area in the interior of the sensor element which is electrically conductively connected to a contact surface situated in the second end area on the outer surface of the sensor element, the electrically conductive connection between the functional element and the contact surface having a strip conductor running essentially in the longitudinal direction in the interior of the sensor element; and
a reference gas channel running essentially in the longitudinal direction of the sensor element and communicating with a reference gas outside of the sensor element via a reference gas opening;
wherein the strip conductor and the reference gas channel are situated in such a way that at least a partial overlap occurs between the strip conductor and the reference gas channel when viewed in a top view of the sensor element, and wherein the strip conductor, at the end facing away from the first end area of the sensor element, runs at an angle of not more than 25° relative to the outer side of the sensor element;
wherein the electrically conductive connection between the functional element and the contact surface has a feedthrough which runs essentially perpendicularly to the longitudinal direction of the sensor element, the feedthrough including a conductive coating of the radial wall of a via hole of the sensor element, and the reference gas channel being situated without overlap with the feedthrough when viewed in the top view of the sensor element;
wherein the functional element is an electric resistance heater which has an electrical resistance of a maximum of 30 Ohms at 20° C.; and
wherein the resistance heater is electrically conductively connected to two contact surfaces situated in the second end area on the outer surface of the sensor element, the two electrically conductive connections between the resistance heater and the contact surfaces each having a strip conductor running essentially in the longitudinal direction in the interior of the sensor element, the strip conductors and the reference gas channel being situated in such a way that in a top view of the sensor element, at least a partial overlap occurs respectively between at least one of the strip conductors and the reference gas channel, and, at the ends of the strip conductors facing away from the first end area of the sensor element, the strip conductors run at an angle of not more than 25° relative to the outer side of sensor element.

7. The sensor element as recited in claim 6, wherein the electrically conductive connections between the resistance heater and the contact surfaces each have a feedthrough which runs essentially perpendicularly to the longitudinal direction of the sensor element, the feedthroughs each including a conductive coating of the radial wall of a via hole of the sensor element, and the reference gas channel being situated without overlap with at least one of the feedthroughs when viewed in the top view of the sensor element.

8. A sensor element for detecting a physical property of a gas, comprising:
a first end area and a second end area situated diametrically opposite in the longitudinal direction of the sensor element;
a functional element in the first end area in the interior of the sensor element which is electrically conductively connected to a contact surface situated in the second end area on the outer surface of the sensor element, the electrically conductive connection between the functional element and the contact surface having a strip conductor running essentially in the longitudinal direction in the interior of the sensor element;
a reference gas channel running essentially in the longitudinal direction of the sensor element and communicating with a reference gas outside of the sensor element via a reference gas opening;
wherein the strip conductor and the reference gas channel are situated in such a way that at least a partial overlap occurs between the strip conductor and the reference gas channel when viewed in a top view of the sensor element, and wherein the strip conductor, at the end facing away from the first end area of the sensor element, runs at an angle of not more than 25° relative to the outer side of the sensor element;

wherein the electrically conductive connection between the functional element and the contact surface has a feedthrough which runs essentially perpendicularly to the longitudinal direction of the sensor element, the feedthrough including a conductive coating of the radial wall of a via hole of the sensor element, and the reference gas channel being situated without overlap with the feedthrough when viewed in the top view of the sensor element;

wherein the functional element is a two-dimensionally configured cermet electrode which communicates with the exterior space of the sensor element via the reference gas channel;

wherein an overlap occurs which extends locally in the transverse direction of the sensor element across not less than 5% of at least one of the local width of the reference gas channel and the local width of the strip conductor.

9. A sensor element for detecting a physical property of a gas, comprising:

a first end area and a second end area situated diametrically opposite in the longitudinal direction of the sensor element;

a functional element in the first end area in the interior of the sensor element which is electrically conductively connected to a contact surface situated in the second end area on the outer surface of the sensor element, the electrically conductive connection between the functional element and the contact surface having a strip conductor running essentially in the longitudinal direction in the interior of the sensor element;

a reference gas channel running essentially in the longitudinal direction of the sensor element and communicating with a reference gas outside of the sensor element via a reference gas opening;

wherein the strip conductor and the reference gas channel are situated in such a way that at least a partial overlap occurs between the strip conductor and the reference gas channel when viewed in a top view of the sensor element, and wherein the strip conductor, at the end facing away from the first end area of the sensor element, runs at an angle of not more than 25° relative to the outer side of the sensor element;

wherein the electrically conductive connection between the functional element and the contact surface has a feedthrough which runs essentially perpendicularly to the longitudinal direction of the sensor element, the feedthrough including a conductive coating of the radial wall of a via hole of the sensor element, and the reference gas channel being situated without overlap with the feedthrough when viewed in the top view of the sensor element;

wherein the functional element is a two-dimensionally configured cermet electrode which communicates with the exterior space of the sensor element via the reference gas channel;

wherein an overlap occurs which extends locally in the transverse direction of the sensor element across 100% of at least one of the local width of the reference gas channel and the local width of the strip conductor.

10. A sensor element for detecting a physical property of a gas, comprising:

a first end area and a second end area situated diametrically opposite in the longitudinal direction of the sensor element;

a functional element in the first end area in the interior of the sensor element which is electrically conductively connected to a contact surface situated in the second end area on the outer surface of the sensor element, the electrically conductive connection between the functional element and the contact surface having a strip conductor running essentially in the longitudinal direction in the interior of the sensor element;

a reference gas channel running essentially in the longitudinal direction of the sensor element and communicating with a reference gas outside of the sensor element via a reference gas opening;

wherein the strip conductor and the reference gas channel are situated in such a way that at least a partial overlap occurs between the strip conductor and the reference gas channel when viewed in a top view of the sensor element, and wherein the strip conductor, at the end facing away from the first end area of the sensor element, runs at an angle of not more than 25° relative to the outer side of the sensor element;

wherein the electrically conductive connection between the functional element and the contact surface has a feedthrough which runs essentially perpendicularly to the longitudinal direction of the sensor element, the feedthrough including a conductive coating of the radial wall of a via hole of the sensor element, and the reference gas channel being situated without overlap with the feedthrough when viewed in the top view of the sensor element;

wherein the strip conductor has a selected width in at least one of (i) the area in which the strip conductor runs at an angle, and (ii) the area in which the strip conductor intersects with an edge of the reference gas channel when viewed in a top view of the sensor element, wherein the selected width is greater than a width of an area of the strip conductor facing the exhaust gas by at least 25%.

* * * * *